(12) United States Patent (10) Patent No.: US 7,415,902 B2
Baklanov et al. (45) Date of Patent: Aug. 26, 2008

(54) METHOD FOR THE QUANTIFICATION OF HYDROPHILIC PROPERTIES OF POROUS MATERIALS

(75) Inventors: Mikhail Baklanov, Veltem-Beisem (BE); Konstantin Mogilnikov, Novosibirsk (RU); Quoc Toan Le, Belgrade (BE)

(73) Assignee: Interuniversitair Microelektronica Centrum (IMEC vzw), Leuven (BG)

( * ) Notice: Subject to any disclaimer, the term of this patent is extended or adjusted under 35 U.S.C. 154(b) by 316 days.

(21) Appl. No.: 11/404,440

(22) Filed: Apr. 13, 2006

(65) Prior Publication Data

US 2006/0254374 A1 Nov. 16, 2006

Related U.S. Application Data

(60) Provisional application No. 60/680,665, filed on May 12, 2005.

(51) Int. Cl.
*G01N 7/02* (2006.01)
(52) U.S. Cl. ......................................... 73/866; 356/369
(58) Field of Classification Search ........................ None
See application file for complete search history.

(56) References Cited

U.S. PATENT DOCUMENTS 6,208,014 B1 3/2001 Wu et al. ..................... 257/629
6,435,008 B2 * 8/2002 Baklanov et al. ................ 73/38

2002/0022378 A1 2/2002 Baklanov et al. ............ 438/784

OTHER PUBLICATIONS

Galindo et al., "Systematic positron study of hydrophilicity of the internal pore surface in ordered low-*k* silica thin films", Materials Science and Engineering B, Elsevier Sequoia, vol. 102, No. 1-3, pp. 403-408 (Sep. 15, 2003).

Revol et al., "Porosimetry Measurements on Low Dielectric Constant—Thin Layers by Coupling Spectroscopic Ellipsometry and Solvent Adsorption-Desorption", Journal of Porous Materials, vol. 12, No. 2, pp. 113-121 (Apr. 2005).

Quoc Toan Le et al., "Removal of Plasma-Modified Low-*k* Layer Using Dilute HF: Influence of Concentration", The Electrochemical Society, Inc., Electrochemical and Solid-State Letters 8 (7), pp. F21-F24 (2005).

Mannaert et al., "Minimizing plasma damage and in situ sealing of ultralow-*k* dielectric films by using oxygen free fluorocarbon plasmas", American Vacuum Society, J.Vac. Sci. Technol. B 23(5), pp. 2198-2202 (Sep./Oct. 2005).

Extended European Search Report Application No. EP 05 01 5412, for Interuniversitaire Microelectronica Centrum vzw, dated Jan. 24, 2006.

* cited by examiner

*Primary Examiner*—Robert R Raevis
(74) *Attorney, Agent, or Firm*—McDonnell Boehnen Hulbert & Berghoff LLP

(57) ABSTRACT

Methods for the quantification of hydrophilic properties of a porous material, as well as determining a depth of damage of a porous material are disclosed. An example method includes performing a first ellipsometric measurement on the porous material using a first adsorptive having a first wetting angle. The example method further includes performing a second ellipsometric measurement on the porous material using a second adsorptive having a second wetting angle, wherein the first and second wetting angles are different towards the porous material. The hydrophilic properties of the porous material are determined based, at least in part, on the first and second ellipsometric measurements.

10 Claims, 9 Drawing Sheets

METHOD FOR THE QUANTIFICATION OF HYDROPHILIC PROPERTIES OF POROUS MATERIALS

CROSS REFERENCE TO RELATED APPLICATIONS

This application claims benefit, under 35 U.S.C. § 119(e), of U.S. Provisional Patent Application 60/680,665, which was filed on May 12, 2005. This application also claims priority to European Patent Application EP 05015412.9 filed on Jul. 15, 2005. The entire disclosures of U.S. Provisional Application 60/680,665 and European Application EP 05015412.9 are incorporated herein by reference.

FIELD

The present disclosure is related to methods for the quantification of hydrophilic properties of porous materials, for example, low-k materials having pores. An example method may also be used for determining depth of damage of such porous materials after patterning.

BACKGROUND

One critical issue in integration of porous materials, such as e.g. low-k materials, during semiconductor processing is the degradation of e.g. their dielectric properties during plasma etching and/or resist stripping. The plasmas used during such processes typically comprise oxygen-containing species. The main reason for degradation of the dielectric properties of porous materials is the removal of carbon containing hydrophobic groups by using these oxygen containing plasmas.

Carbon depletion occurs when, for example, a Si—$CH_3$ bond is broken and the carbon is replaced by a silicon-dangling bond. This carbon depletion results in the formation of silanol (Si—OH) through a variety of intermediate reactions. This leads to an increase in k-value for the damaged portion of the porous material and converts the inherently hydrophobic low-k material into a hydrophilic material. Subsequent adsorption of moisture, e.g. water, or other polar molecules having high polarizability, mediated by hydrogen bonding, can significantly increase the effective k-value of the material, e.g. to a k-value>>80. Degree and depth of plasma damage depends on the pore size and the pore connectivity of the porous material and therefore, ultra low-k materials with e.g. k-value lower than 2.6, which normally have a relatively large pore size, suffer much more from this plasma damage than micro-porous materials with a k-value of higher than 2.6. The extent of the damaged portion of the dielectric material at sidewalls of etched material is also expected to increase as the porosity of the porous material increases, and the extent of such damage on overall electrical performance gains importance as the spacing between interconnect lines shrinks. Therefore, sidewall dielectric damage has a major impact on the performance of advanced interconnects, and a reliable analysis method for evaluating the extent of such damage is desirable.

In general, the depth and profile of carbon depletion is evaluated using complicated analytical techniques like, for example, Time-of-Flight Secondary Ion Mass Spectroscopy (TOF-SIMS), X-ray photoelectron spectroscopy (XPS), Energy Filter transmission Electron microscopy (EFTEM) etc., or by using the so called HF-dip test. TOF-SIMS is a type of SIMS in which an ultra-low current incident ion beam is used and by which information regarding chemical composition of the outermost surface of solids can be obtained. EFTEM is a technique that detects the variation of the atomic concentrations of elements such as C, O and Si through the cross-section of a feature.

Using TOF-SIMS, it is assumed that only the carbon concentration is responsible for the hydrophobic properties that define the dielectric constant of the film, independent of how they are bonded and integrated in the porous material structure. TOF-SIMS data for determining the depth of low-k damage are related to the carbon concentration in the surface region of the low-k porous material and these data are compared with the carbon concentration in the bulk of the low-k material. The carbon depletion in the surface region after etching and stripping is then an indication of the low-k damage. However when such low-k materials, e.g. films, are subjected to HF dip test there is no clear correlation between carbon depletion and plasma damage.

A HF dip test is based on the fact that damaged low-k dielectric material shows a higher etch rate than undamaged material. Normally this test more directly reflects the hydrophilic properties of the porous material but an autocatalytic mechanism of interaction of HF with $SiO_2$ makes this test not reliable because the etch rate and the calculated depth of damage depends on the HF concentration.

Carbon depletion cannot always directly be correlated with plasma damage. For example, when a highly polymerizing chemistry is used (e.g. CxFyHz plasma), the carbon depletion is compensated by the deposition of CFx polymers resulting in equal or increased carbon concentrations in the low-k porous material surface. According to traditional interpretation of TOF-SIMS results, this surface should be the most hydrophobic (no "damage"). However, HF dip tests show a larger etch rate of this sample in comparison with an undamaged low-k reference material, which in general is pristine. Therefore, the fluorocarbon polymer that is formed during the etching process and that fills the pores of the porous material is not able to provide the same hydrophobic properties as the original hydrophobization agents. These facts show the importance for the development of special measurement procedures that give more direct analysis on the degree of internal hydrophilization related to plasma damage.

In addition, all the existing methods described above and other methods available in the prior art are destructive and/or very complicated and do not give information directly correlated with loss of hydrophobicity, which has the largest effect on the dielectric properties of the porous material. Thus, existing methods to determine low-k damage have serious drawbacks and shortcomings. A method that allows for determining the depth of damage and exact hydrophobicity of low-k material is desirable. Additionally, there is a need for a simple non-destructive method for use in developing and screening different low-k materials, especially for ultra low-k materials that will be used for future technologies.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are given by way of example and meant to be illustrative, not limiting in scope. In various embodiments, one or more of the above-described problems have been reduced or eliminated, while other embodiments are directed to other improvements.

Examples of non-destructive methods for the quantification of hydrophilic properties of a porous material are disclosed. For instance, an example method is disclosed for the quantification of hydrophilic/hydrophobic properties of a porous material, these hydrophilic/hydrophobic properties can be a measure for the degree of damage of a porous material. The material may be a porous low-k material or an ultra low-k material. The example method makes use of adsorption/desorption characteristics within the pores of the porous material. Furthermore the method makes use of first and second adsorptives with different contact angles (also referred to as wetting angle) towards an inner surface of the pores of the porous material. In the example method, the first adsorptive is an adsorptive with a contact or wetting angle substantially equal to zero and the second adsorptive is an adsorptive with a substantially non-zero contact or wetting angle with regard to the porous material, having polar properties. Examples of first adsorptives (with a substantially zero contact angle towards low-k materials and porous membranes comprising organic molecules) are nitrogen, toluene, methanol and benzene; these adsorptives show good wettability with porous materials, e.g. low-k materials. Examples of the second adsorptives (with non-zero contact angle towards low-k materials and porous membranes comprising organic molecules) are water, thionyl ($SOCl_2$) or any other suitable inorganic solvent having a non-zero contact angle towards low-k materials and porous membranes comprising organic molecules.

The example method provides for the quantification of hydrophilic properties of a porous material and includes at least a first and a second ellipsometric measurement, the first ellipsometric measurement is performed with a first adsorptive and the second ellipsometric measurement is performed with a second adsorptive, the first and second adsorptive having different wetting angles towards the porous material.

In another example method, a method is provided for determining the degree of damage to a porous material, e.g. a low-k material, and more specifically to determine the internal surface energy (effective contact angle), degree and depth of damage within the porous material, e.g. low-k material. Damage is defined here as loss of hydrophobicity of the porous material, e.g. low-k material, that is related to plasma etch and/or strip processes. More specifically a method is disclosed that includes at least three ellipsometric measurements. In this example method, the ellipsometric measurements are ellipsometric adsorption measurements. As with the first example method discussed above, a first and second adsorptive are used in this method, where each adsorptive has a different wetting angle with respect to an inner surface of the pores of the porous material. For instance, the first adsorptive is an adsorptive with a contact or wetting angle towards the porous materials which is substantially equal to zero and the second adsorptive is an adsorptive with substantially non-zero contact (wetting) angle towards the porous material, and having polar properties.

In addition to the steps of the first example described above, this second example method further includes a third ellipsometric measurement on the porous material before damage treatment using the second adsorptive having a second wetting angle toward the porous material. For purposes of this disclosure, damage treatment means processing steps that result in damage to the porous material (e.g., plasma etch steps). The third ellipsometric measurement is performed on a reference porous material, e.g. the porous material before damage treatment or a reference low-k film, with almost no hydrophilic properties. Often pristine dielectric material is used for the reference material. The third ellipsometric measurement in this method also makes use of the second adsorptive having polar molecules such that the intrinsic hydrophilic properties within the pores of the reference material, e.g. a reference low-k film, can be obtained.

Such a method may be used to determine the damage of porous materials, e.g. low-k films, after dry etch and strip processing. For instance, the low-k material may be a SiOC (H) material, such as an ultra low-k material having pore sizes 2 to 10 nm. Using such a method, the quantification of the hydrophobicity of the porous material may be used for determining the depth of damage caused to the porous material by an etch and/or stripping process.

BRIEF DESCRIPTION OF THE DRAWINGS

Example embodiments are illustrated in referenced figures of the drawings. It is intended that the embodiments and figures disclosed herein are to be considered illustrative rather than restrictive.

DETAILED DESCRIPTION

Overview

During particular semiconductor processing steps for the manufacture of devices including porous materials, such as etching and/or stripping steps, the porous materials may be damaged. Porous materials, for example, porous low-k films, may lose organic hydrophobic groups during plasma etch and/or strip processes. As a result, they become hydrophilic and they adsorb moisture and other polar molecules that affect their dielectric properties. The degree of plasma damage caused to the porous material, e.g., low-k material, during these plasma etch and/or strip processes is currently evaluated by using techniques such as e.g. depth-profile analysis using XPS, TOF-SIMS, EFTEM or others.

In these methods, plasma damage is correlated with carbon depletion. However, as already discussed above, carbon depletion cannot always be directly correlated with plasma damage. For example, when a highly polymerizing plasma is used such as a, e.g., CxFyHz plasma, the carbon depletion is compensated by the deposition of CFx polymers but the porous material should have different properties in comparison with an undamaged reference porous material, e.g.

porous low-k material, in order to determine the extent of damage. Often pristine material is used as undamaged reference low-k material.

An alternative current approach is a HF dip test that is based on the fact that plasma damage has a correlation with the depth of etching. The HF etch depth, however, strongly depends on HF concentration because of auto catalytic etch mechanism of Silica by HF.

Figure 1:
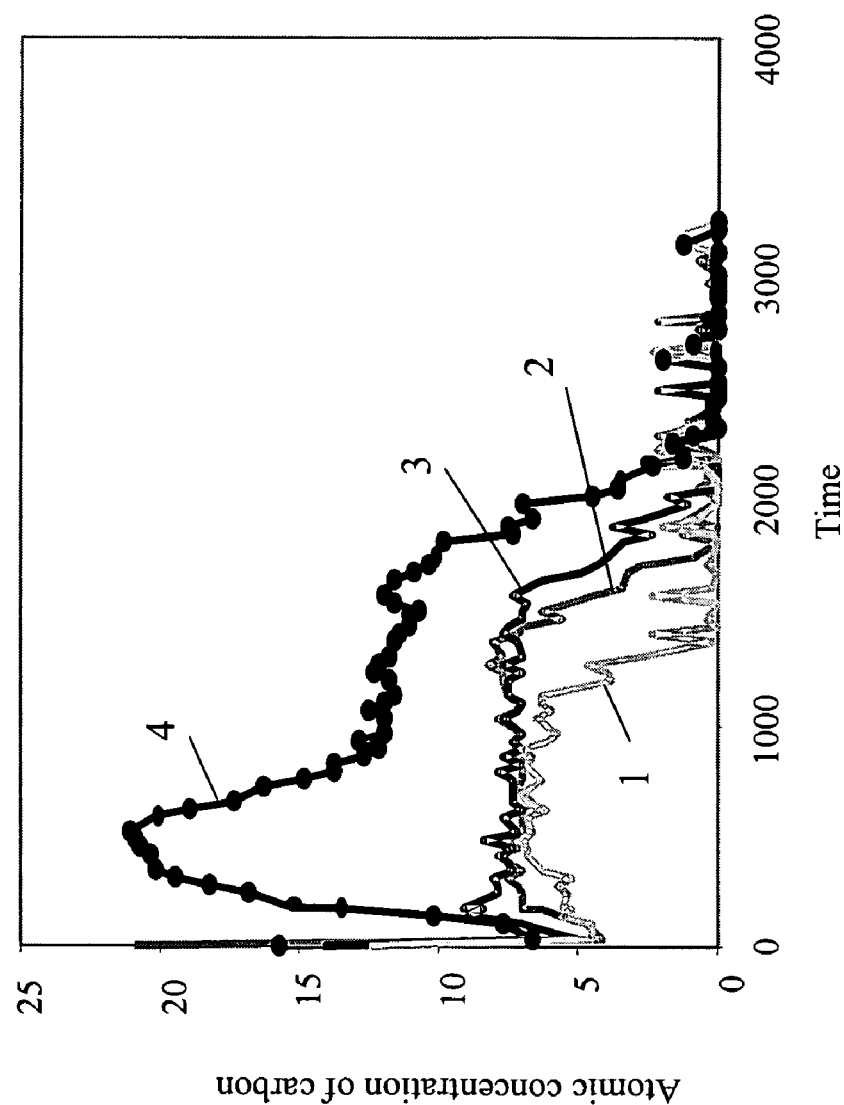
FIG. 1 shows TOF-SIMS data for atomic concentration of carbon as a function of time for a SiOC(H) low-k material after etching with a $CF_4$ comprising plasma, a $C_4F_8$ comprising plasma at low power, a $C_4F_8$ comprising plasma at intermediate power and a $C_4F_8$ comprising plasma at high power.

FIG. 1 shows TOF-SIMS data for the atomic concentration of carbon as a function of etching, e.g. ion sputtering time, which is proportional to depth of etching for a SiOC(H) low-k material after etching with a $CF_4$ comprising plasma (curve 1), a $C_4F_8$ comprising plasma at low power (e.g. 300 W at 27 MHz and 600 W at 2 MHz) (curve 2), a $C_4F_8$ comprising plasma at intermediate power (e.g. 800 W at 27 MHz and 1800 W at 2 MHz) (curve 3) and a $C_4F_8$ comprising plasma at high power (1000 W at 27 MHz and 2000 W at 2 MHz) (curve 4).

As shown in FIG. 1, a $CF_4$ based plasma (curve 1) results in, for this example, the most significant carbon depletion in the surface region. High power $C_4F_8$ based plasma (curve 2) also shows a decrease in carbon concentration, but to a lower extent, in the surface region of the low-k material. According to TOF-SIMS interpretation of the results, this corresponds to a decrease in the depth of damage. Intermediate power $C_4F_8$ based plasma (curve 3) shows a small surface region indicating a decrease in carbon concentration and some enrichment of carbon concentration. Low power $C_4F_8$ based plasma (curve 4) shows a significant increase of carbon concentration in the surface region and bulk of the low-k material, especially in the region that corresponds to 30-50 nm from the top surface of the film. This can be determined from the fact that the depth of etching is proportional to the time of etching, e.g. ion sputtering. If the film thickness and the time of etching are known, the depth of etching can be calculated as a function of time, assuming that the etch rate is constant.

However, the observation of the increase of the carbon concentration in the damaged material, which is normally higher compared to the carbon concentration in a non-damaged material, in the example given pristine reference material, is not related to the carbon concentration of the original SiOC(H) material (NCS (Nanocrystalline Silica) from CCIC, Japan, with initial porosity of 31%) but is caused by CFx polymers, also referred to as hydrofluorocarbon polymers, deposited during etching. These CFx polymers are a by product of etch process and not indicative of damage to the porous material. For instance, according to the traditional interpretation of TOF-SIMS results, this material should be the most hydrophobic (should have no substantially "damage"). However, a HF dip test shows a faster etch rate of this sample in comparison with the reference pristine sample. The deposited CFx polymers tend to increase the k-value of the low-k material or at least change the material properties from hydrophobic (original material) towards hydrophilic. Therefore, the fluorocarbon polymer that is formed during the etching process and that fills the pores of the porous material is not able to provide the same hydrophobic properties as the original hydrophobic groups which are lost during the etching process. The foregoing demonstrates the desirability of a method that provides more direct information on the degree of internal hydrophilization of a porous material, for example low-k material, and more specifically the hydrophilization within the pores of the porous material, e.g., the low-k material.

Method for Determining Hydrophilic/Hydrophobic Properties of a Porous (Low-k) Material Hereinafter, an example method for the determination of hydrophilic and/or hydrophobic properties of porous materials of low-k materials will be described. However, it will be appreciated that this example is illustrative and is not intended to be limiting in scope to the claims. For instance, the example method according may also be applied to other porous materials such as, for example, porous membranes (e.g. zeolite membranes).

The example method provides for the determination of hydrophilic and/or hydrophobic properties of a porous material, such as low-k materials or porous membranes. The porous material may be a porous low-k material or an ultra low-k material. The example method makes use of adsorption and/or desorption characteristics within the pores of the porous material. By performing different ellipsometric porosimetry measurements (hereinafter referred to as "ellipsometric measurements") while making use of different adsorptives or gaseous substances having different contact angles (also referred to as wetting angles) towards the porous material, it hydrophilic/hydrophobic properties of the porous material are determined.

Ellipsometric measurements are based on analysis of hysteresis loops that appear due to processes of capillary condensation in adsorption and desorption of vapor out of pores of a porous material. The hysteresis loops appear because the effective radius of curvature of a condensed liquid meniscus is different during the adsorption and desorption processes. The adsorptive vapor condenses in pores of the porous material even if the vapor pressure P is less than the equilibrium pressure of a flat liquid surface $P_0$. Dependence of the relative pressure $P/P_0$ on the meniscus curvature is described by the Kelvin equation:

$$\frac{1}{r_1} + \frac{1}{r_2} = -\frac{RT}{\gamma V_L} \ln\left(\frac{P}{P_0}\right) \quad (1)$$

wherein $\gamma$ and $V_L$ respectively are the surface tension and the molar volume of the adsorptive or gaseous substance used. The principal curvature radii $r_1$ and $r_2$ (elliptic radii) define pore sizes. In the case of cylindrical pores, $r_1 = r_2$ and equation (1) may be written as:

$$\ln\left(\frac{P}{P_0}\right) = -\frac{\gamma V_L}{RT}\left(\frac{2}{r_k}\right) \quad (2)$$

wherein $r_k$ is often called the Kelvin radius.

The Kelvin equation (2) directly gives the pore radius, considering that the wetting angle of the adsorptive or gaseous substance with respect to the surface of the porous material is substantially zero. However, according to the invention, adsorptives or gaseous substances with different contact or wetting angles with respect to the porous material are used, and thus the contact or wetting angle has to be taken into account. Therefore, equation (2) becomes:

$$\ln\left(\frac{P}{P_0}\right) = -\cos\theta * \frac{\gamma V_L}{RT} * \left(\frac{2}{r_k}\right) \quad (3)$$

wherein θ is the contact or wetting angle of the adsorptive or gaseous substance with respect to the porous material and $r_k$ is the average radius of the pores present in the porous material. The ellipsometric measurements are performed using single or multiwave length ellipsometry.

Figure 2:
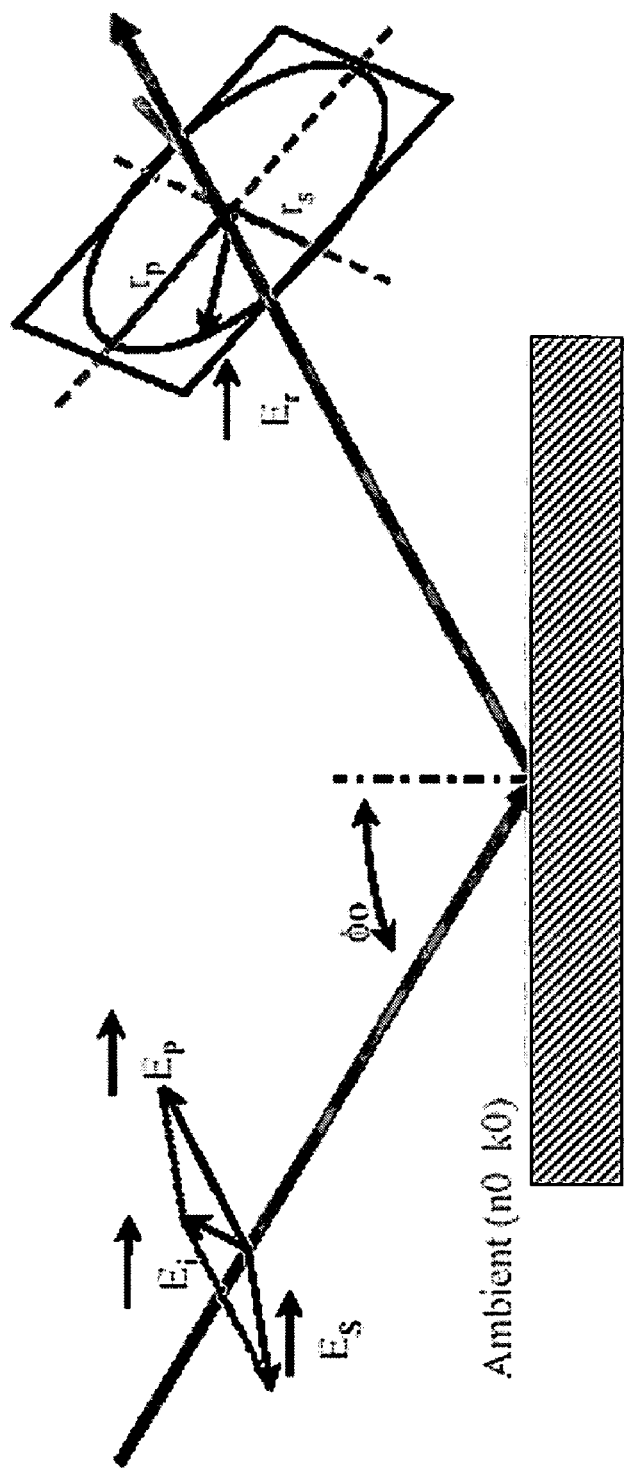
FIGS. 2 and 3 illustrate the principle of an ellipsometric measurement.
Figure 3:
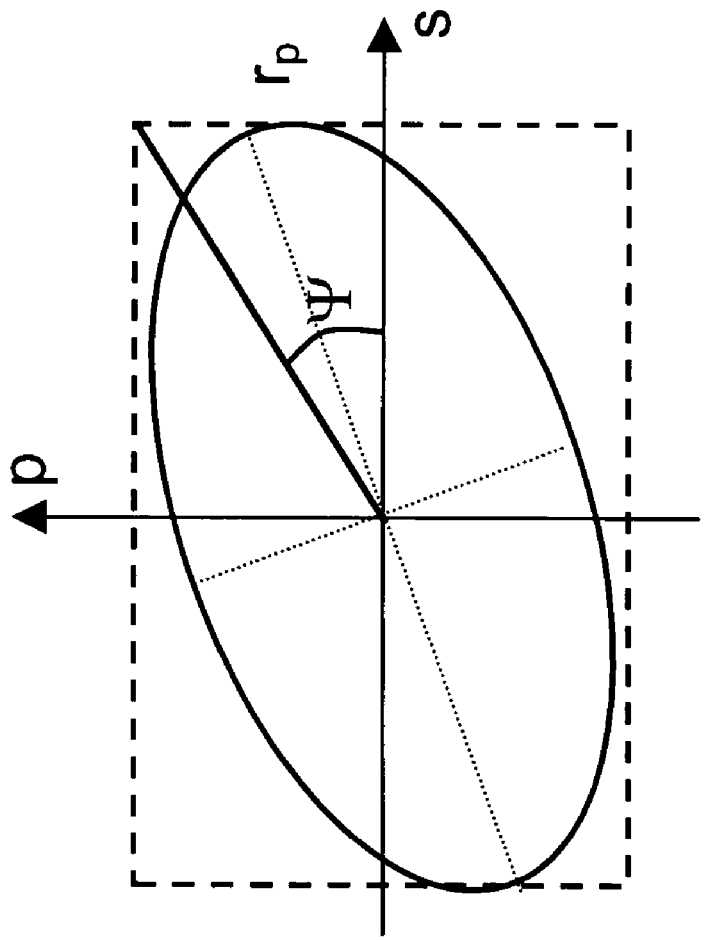

The initial experimental data for the calculation of the adsorption isotherm are the ellipsometric characteristics Δ (phase difference between p-polarized and s-polarized light (see FIG. 2)) and Ψ (illustrated in FIG. 3), as ellipsometric measurements are normally expressed in terms of these parameters:

$$\tan(\Psi) \cdot e^{i\Delta} = \rho = \frac{r_p}{r_s} \quad (4)$$

wherein $r_p$ and $r_s$ are the complex Fresnel reflection coefficients of the sample for p- (in the plane of incidence) and s- (perpendicular to the plane of incidence) polarized light (see FIG. 2). Special software, developed at the Institute of Semiconductor Physics in Novosibirsk, Russia, then allows for the calculation of the change of the refractive index of the porous material during adsorption and desorption. The change of adsorptive volume, or the pore volume, is then calculated from the change of refractive index using the following equation:

$$V = 1 - \frac{B_p}{B_b} = 1 - \left[\frac{(n_p^2 - 1)}{(n_p^2 + 2)}\right] / \left[\frac{(n_b^2 - 1)}{n_b^2 + 2}\right] \quad (5)$$

wherein $n_b$ is the refractive index of the dense part, i.e. the matrix, of material with volume polarizability $B_b$, $n_p$ is the measured refractive index of the pores and $B_p$ is the volume polarizability calculated from $n_p$. The dependence of the adsorptive volume on the relative pressure $P/P_0$ results in an adsorption isotherm.

As already described above, the method according to the first embodiment of the invention makes use of two different adsorptives or gaseous substances, i.e. a first adsorptive or gaseous substance with a first contact or wetting angle with respect to the surface of the porous material to be examined and a second adsorptive or gaseous substance with a second contact or wetting angle with respect to the surface of the porous material to be examined. According to the invention, the first contact or wetting angle is different from the second contact or wetting angle. According to the first embodiment of the invention, the first wetting angle is substantially equal to zero. Where substantially equal to zero means that the first wetting angle may be smaller than 5°, smaller than 3°, or smaller than 1°. The second contact or wetting angle is substantially different from zero. Preferably the difference between the first and second contact or wetting angle may be as high as possible. Preferably, the second contact or wetting angle may be 90° or higher.

Examples of adsorptives with a contact or-wetting angle substantially equal to zero with respect to low-k materials or to porous membranes comprising organic molecules which may be used according to the invention may be e.g. nitrogen, toluene, methanol and benzene. In this case, cos θ=1 (because θ=0) in the Kelvin equation (3) and the adsorption/desorption cycle allows to calculate the volume of adsorbed adsorptive in the pores of the porous material which then corresponds to the volume of open pores present in the porous material, using the method as described above. Examples of adsorptives with a contact angle substantially different from zero with respect to low-k materials or to porous membranes comprising organic molecules may be water, thionyl (SOCl$_2$), or any other suitable inorganic solvent having a non-zero contact angle towards low-k materials or porous membranes comprising organic molecules.

To perform the ellipsometric measurements a substrate having the porous material, e.g. a low-k film, on top of it is located in a pressurize-able chamber filled with the first adsorptive or gaseous substance. Thereafter, the second measurement is performed in the same way but now in a pressurize-able chamber filled with the second adsorptive or gaseous substance.

Hereinafter, the method according to above described preferred embodiments of the invention will be further explained by means of an example. It is to be understood that this example is not limiting the invention. The method according to the first embodiment of the invention may be applied to any porous material such as low-k materials or porous membranes having any degree of porosity.

In the following example, the hydrophilic/hydrophobic properties of a low-k material will be determined. In a first step, a first ellipsometric measurement is performed using e.g. toluene as a first adsorptive. From the measured values of Ψ and Δ the change of refractive index n of the porous material is determined and from that change of refractive index n the change of adsorbed volume of toluene is determined, using the method as described above.

Figure 4:
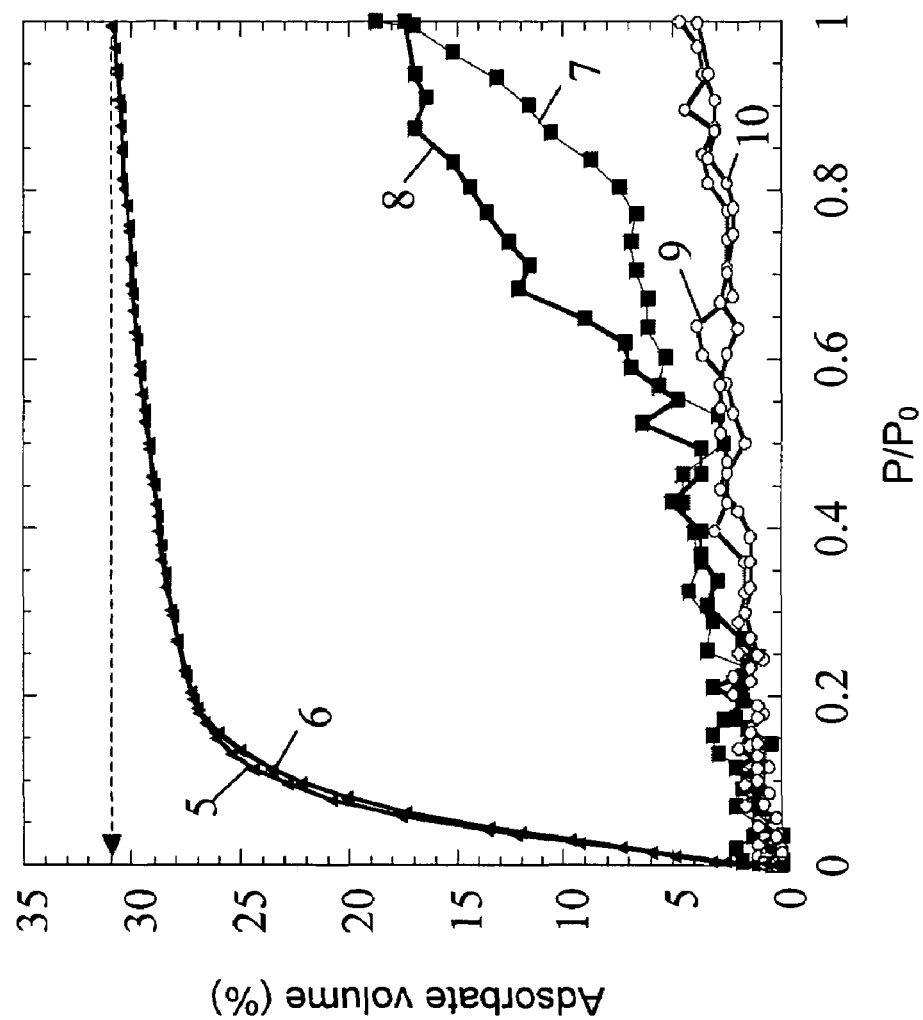
FIG. 4 shows the adsorption/desorption cycle of toluene for a (damaged) low-k film, the adsorption/desorption cycle of water vapor for a (damaged) low-k film and the adsorption/desorption cycle of water vapor for a pristine reference material.

In FIG. 4 the adsorption/desorption cycle of toluene (respectively curve 5 and 6) for the low-k film of the example given is shown. From curves 5 and 6 it can be determined that the low-k film of the example given in FIG. 4 has a porosity of about 31%. This porosity value is determined by the amount of adsorptive adsorbed in the pores of the porous material at a relative pressure $P/P_0$ equal to one or at a pressure $P=P_0$. At this pressure, the adsorptive or gaseous substance is fully condensed into the pores of the porous material, in the example given, in the pores of the low-k material. Therefore, the amount of adsorbed adsorptive equals the amount of pores present in the porous material, in the example given in the low-k material.

It has to be noted that the first step may be performed on at least one of a damaged or an undamaged porous material. Advantageously, the first measurement may be performed to both the undamaged (before processing) and the damaged (after processing) material, because it can occur that processing results in formation defects which may act as pores. Because of that, the porosity of the porous material can increase during processing. In that way, the porosity of the starting material can be determined as well a correct determination of damage caused by the processing steps.

In a second step, the damaged material is submitted to a second ellipsometric measurement using a second adsorptive or gaseous substance with a contact or wetting angle substantially different from zero with respect to the porous material.

Undamaged low-k dielectrics are, in general, hydrophobic which means that in the Kelvin Equation (3) cos θ is close to zero when a polar adsorptive having a contact or wetting angle substantially different from zero with respect to the porous material, in the example given the low-k material, such as, for example, water, is used. Hence, in the case of water as an adsorptive, substantially no water condensation will occur in these porous materials, e.g. low-k films. From the second ellipsometric measurement the values for Ψ and Δ are determined, from which subsequently the change in refractive index of the porous material, in the example given the low-k material, and the change in the amount of adsorbed water are determined, using the method as described above. FIG. 4 furthermore shows the adsorption/desorption cycle of water vapor for a damaged low-k film (respectively curve 7 and 8). From these curves 7, 8 an amount of adsorbed water of about 18.5% is determined. This value is determined by determining the adsorbed water volume at a pressure of $P=P_0$ (or $P/P_0=1$). From the amount of adsorbed water, the concentration of damaged centers can be calculated as follows. From the percentage of adsorbed water, the volume of adsorbed water can be determined. By multiplying the volume of adsorbed water with the density of water, the weight of adsorbed water is obtained. Dividing by the molecular weight of water yields the amount of moles adsorbed water. By multiplying this result with the Avogadro number, the number of centers to which water is adsorbed is achieved.

Furthermore, FIG. 4 illustrates the adsorption/desorption cycle of water vapor for a reference material, which, in the example given, is pristine (respectively curve 9 and 10). The reference material may be seen as a porous material before damaging by means of etching and/or stripping. Insignificant water adsorption in the pristine film shown in FIG. 4 happens without bulk condensation and reflects the presence of only a small amount of centers at which water adsorption (constitutively defective) can occur. If the number of these centers is limited, the contact or wetting angle remains high because the adsorbed water molecules do not form a continuous layer on the wall surface. FIG. 4 shows that the pristine film adsorbs only 4% of water of the total film volume. Measurements on a reference material, e.g., on an undamaged porous material, are performed in order to determine damage introduced by etching and/or stripping processes and to distinguish them from constitutive hydrophilic centers, initially present in the material, from the total amount of measured centers.

However, the situation is different in the case of a damaged low-k film. The surface area of this damaged low-k film becomes hydrophilic due to loss of hydrocarbon groups and therefore the amount of adsorbed water significantly increases. The water adsorption/desorption isotherm for a damaged low-k film is also shown in FIG. 4 (respectively curve 7 and 8, as already indicated above). The water adsorption/desorption isotherm for a damaged low-k film allows for determining the adsorbed amount of water (increase of this value as a result of plasma damage) and the relative pressure that corresponds to the beginning of water condensation. This relative pressure at which water condensation starts allows the calculation of the internal contact angle using equation (4).

To determine the degree of hydrophilization (hydrophilic/hydrophobic properties) two Kelvin equations (6), (7) are combined, the first Kelvin equation (6) with values obtained after the first ellipsometric measurement with adsorptive having substantially zero contact angle with respect to the porous material (e.g. toluene, benzene) and the second Kelvin equation (7) with values obtained after the second ellipsometric measurement with adsorptive having a non-zero contact angle with respect to the porous material, where the second adsorptive has polar properties (e.g. water). Combination of the two Kelvin equations (6), (7) may be performed as described below.

$$\ln\left(\frac{P}{P_0}\right) = -\cos\theta^* \, \frac{\gamma_L V_L}{RT} * \left(\frac{2}{r}\right) \quad (3)$$

$$\ln\left(\frac{P}{P_0}\right)_{a1} = -\frac{\gamma_{a1} V_{La1}}{RT} * \left(\frac{2}{r}\right) \quad (6) \qquad \ln\left(\frac{P}{P_0}\right)_{a2} = -\cos\theta^* \, \frac{\gamma_{a2} V_{La2}}{RT} * \left(\frac{2}{r}\right) \quad (7)$$

Combination of these Kelvin equations (6) and (7) allows for determining the effective "contact angle" of the adsorptive or gaseous substance with "non-zero" contact angle, such as water, with respect to the porous material. The effective contact or wetting angle gives information about surface energy, which is correlated to the hydrophilic properties of the porous material. The contact angle is a measure of the surface energy. The equilibrium situation is expressed by Young's equation:

$$\gamma_{SV} - \gamma_{SL} = \gamma_{LV} \cos\theta \quad (8)$$

where $\gamma_{SV}$, $\gamma_{SL}$ and $\gamma_{LV}$, respectively, are the surface energy of the solid, the surface energy of the interface and the surface energy of water. Using equation (8) the difference between the two quantities at the left hand side can be determined. In order to separate these two quantities, e.g., to separate surface energy of the solid and surface energy of the interface, certain models, based on how liquids and solids adhere together is used.

Equation (6) is the Kelvin equation for the first adsorptive or gaseous substance with a first contact or wetting angle that is substantially equal to zero. Equation (7) is the Kelvin equation for the second adsorptive or gaseous substance with a non-zero second contact or wetting angle. In equations (6) and (7) the subscripts a1 and a2 respectively stand for the first adsorptive or gaseous substance and the second adsorptive or gaseous substance. The result of the combination of equation (6) and (7) is:

$$\theta = \arccos\left\{\left[\ln\left(\frac{P}{P_0}\right)_{a2} \middle/ \ln\left(\frac{P}{P_0}\right)_{a1}\right] \cdot \left(\frac{\gamma_{a1} \cdot V_{La1}}{\gamma_{a2} \cdot V_{La2}}\right)\right\} \quad (9)$$

The method described above allows for determining the effective contact angle of the porous material, which is very difficult to practically measure by any other method. Moreover, the effective contact angle directly reflects the hydrophilic/hydrophobic properties that are important for the k-value of the porous material, e.g. low-k material. The difference between the method of the invention and state of the art techniques such as TOF-SIMS/XPS is that the method of this invention does not use any assumptions, such as identity of the carbon depletion and degree of hydrophilization. Furthermore, the example method is not destructive to the porous material, in contrast with existing methods.

As described above, to determine the hydrophilic/hydrophobic properties of porous materials, e.g., Low-k films having pores, an example method includes at least two ellipsometric measurements with use of a first and second adsorptive, where each adsorptive has a different contact or wetting angle with respect to the porous material. In certain embodiments, these ellipsometric measurements may be performed at pressures changing from zero to the equilibrium vapor pressure of the adsorptives used. As previously discussed, for the example method, the first adsorptive may be an adsorptive with a contact or wetting angle substantially equal to zero and the second adsorptive may be an adsorptive with a non-zero contact or wetting angle comprising polar molecules.

Examples of the first adsorptives (with contact angle substantially equal to zero with respect to the porous material) may, in the case of low-k materials and porous membranes comprising organic molecules, be nitrogen, toluene, methanol and benzene, These adsorptives show good wettability with porous materials such as porous low-k materials and porous membranes comprising organic molecules.

Examples of the second adsorptives with non-zero contact or wetting angle with respect to low k-materials or porous membranes comprising organic molecules is water, $SOCl_2$ or any other suitable inorganic solvent having a non-zero contact angle towards low-k materials and porous membranes comprising organic molecules.

A Method for the Quantification of Low-k Damage or Depth of Damage of a Low-k Film In an alternative embodiment, a method for determining depth of damage in a porous material, e.g. a low-k film, is provided. The method includes determining the internal surface energy or effective contact angle, degree and depth of damage in a porous material, such as a low-k material, and more specifically to determine the depth of damage within a porous material, such as a low-k material, after plasma etch and/or strip processing. Plasma damage is defined here as a loss of hydrophobicity of the porous material due to loss of organic hydrophobic groups, e.g., in case of low-k materials, hydrocarbon groups. The damage may result from plasma etch and/or strip processing of the porous material.

To determine the depth of damage within a porous material in this example method, a film formed of a porous low-k film, that includes two layers with different properties, is used. The first, or top layer presents the damaged area of the porous low-k film. The first or top layer is more hydrophilic than the second or bulk layer of the porous low-k film. The bulk layer is considered not to be damaged. Taking into account this fact, the depth of plasma damage within such a porous low-k film may be determined.

The amount of adsorbed water within the pores of the porous low-k material, in like fashion as discussed above, may be used in this example method to calculate the degree of damage and, more specifically, to calculate the depth of damage within the porous low-k film.

To determine the depth of damage within a damaged low-k film, this example method includes least three ellipsometric measurements to determine the adsorption characteristics within the pores of the porous film at pressures ranging from zero to the equilibrium vapor pressure of the adsorptives used. To perform these ellipsometric measurements, a substrate having the porous low-k film on top of it is located in a pressurize-able chamber filled with the first adsorptive (which may be a gaseous substance). Thereafter, the second measurement is performed in the same way as described above but in the pressurize-able chamber filled with the second adsorptive (which may be a gaseous substance).

For the first ellipsometric measurement performed on the undamaged porous low-k material, a first adsorptive or gaseous substance is used with a first contact or wetting angle towards the porous material which is substantially equal to zero, such that the porosity and/or pore size of the porous low-k film can be obtained. For purposes of the examples described herein, substantially equal to zero means that the first contact or wetting angle may be lower than 5°, lower than 3° of lower than 1°. Determination of pore size in adsorption porosimetry (e.g., using Ellipsometric Porosity (EP) measurements) is based on the Kelvin equation (2), which correlates the relative pressure with the pore radius.

To make such measurements accurate, an adsorptive or gaseous substance with a contact or wetting angle substantially equal to zero with respect to the porous film surface is used.

Examples of such adsorptives are nitrogen, toluene, methanol and benzene. In this case $\cos\theta=1$ (because $\theta=0°$) in the Kelvin equation (3) and adsorption/desorption cycle allows for calculating the volume of adsorbed toluene (open pores volume). Preferably the contact or wetting angle of the chosen adsorptive or gaseous substance may be substantially the same for both the reference non-damaged material, e.g. pristine material, and the damaged low-k material. The value obtained from this measurement is referred to as $P_{a1}$ or porosity of the porous low-k film measured by an adsorptive or gaseous substance with contact or wetting angle substantially equal to zero.

In the example method, a second ellipsometric measurement is performed on a damaged porous low-k film, where a second adsorptive or gaseous substance is used with a second contact or wetting angle towards the porous material. The second adsorptive may include polar molecules, such that the adsorption of the second gaseous substance within the pores of the damaged low-k film can be measured. The second gaseous substance or adsorptive may have a contact angle equal to or higher than 90°. By way of example, the second gaseous substance may be water, $SOCl_2$ and any other suitable inorganic solvent having a non-zero contact angle towards low-k materials and porous membranes comprising organic molecules. The value obtained from this second ellipsometric measurement is referred to as $P_{a2,1}$, or porosity of the damaged porous low-k film measured by the second adsorptive or gaseous substance, e.g. water or other polar substances.

In this example method, a third ellipsometric measurement is performed on the undamaged low-k film (also referred to as a reference low-k film or "pristine material"), e.g., on the porous low-k film before it is submitted to an etching and/or stripping process that results in damage to the film. The undamaged low-k film has almost no hydrophilic properties with the second gaseous substance (adsorptive), such that adsorption of the second gaseous substance within the pores of the reference low-k film can be obtained. The value obtained from this third ellipsometric measurement is referred to as $P_{a2,2}$ or porosity of the undamaged low-k film measured by water or other polar substances.

The three ellipsometric measurements described above are combined in the following equation (10), which is then used to determine the depth of damage within a low-k film:

$$P_{a2,2} * d_0 = P_{a1} * d + P_{a2,1} * (d_0 - d) \tag{10}$$

wherein $P_{a2,2}$ is the porosity (volume of the adsorbed liquid) of the damaged porous low-k film measured by a polar gaseous substance, $P_{a2,1}$ is porosity (volume of the adsorbed liquid) of the porous low-k film before damage (measured by water); $P_{a1}$ is the porosity of the undamaged porous low-k film measured using toluene; $d_0$ is the film thickness and d is the depth of wetting.

As discussed above, the value $P_{a1}$ is obtained from the first ellipsometric measurement performed on the low-k film with a first gaseous substance with contact or wetting angle towards the porous material substantially equal to zero such that the porosity and/or pore size of the low-k film can be obtained. The first adsorptive may be nitrogen, toluene, methanol or benzene. The value $P_{a2,2}$ is obtained from the second ellipsometric measurement performed on the damaged low-k film with a second adsorptive or gaseous substance with polar molecules. The second adsorptive or gaseous substance may be water. The value $P_{a2,1}$ is obtained from the third ellipsometric measurement performed on the undamaged low-k film (before plasma etch and/or stripping) with the second adsorptive or gaseous substance with polar molecules.

EMPIRICAL EXAMPLES

Example 1

Determination of the Amount of Water Adsorbed in a Porous Low-k Film

FIGS. 5A-5E show adsorption/desorption isotherms for an undamaged reference low-k material (pristine) and a SiOC (H) low-k material (NCS) after different plasma etch processes.

Figure 5A:
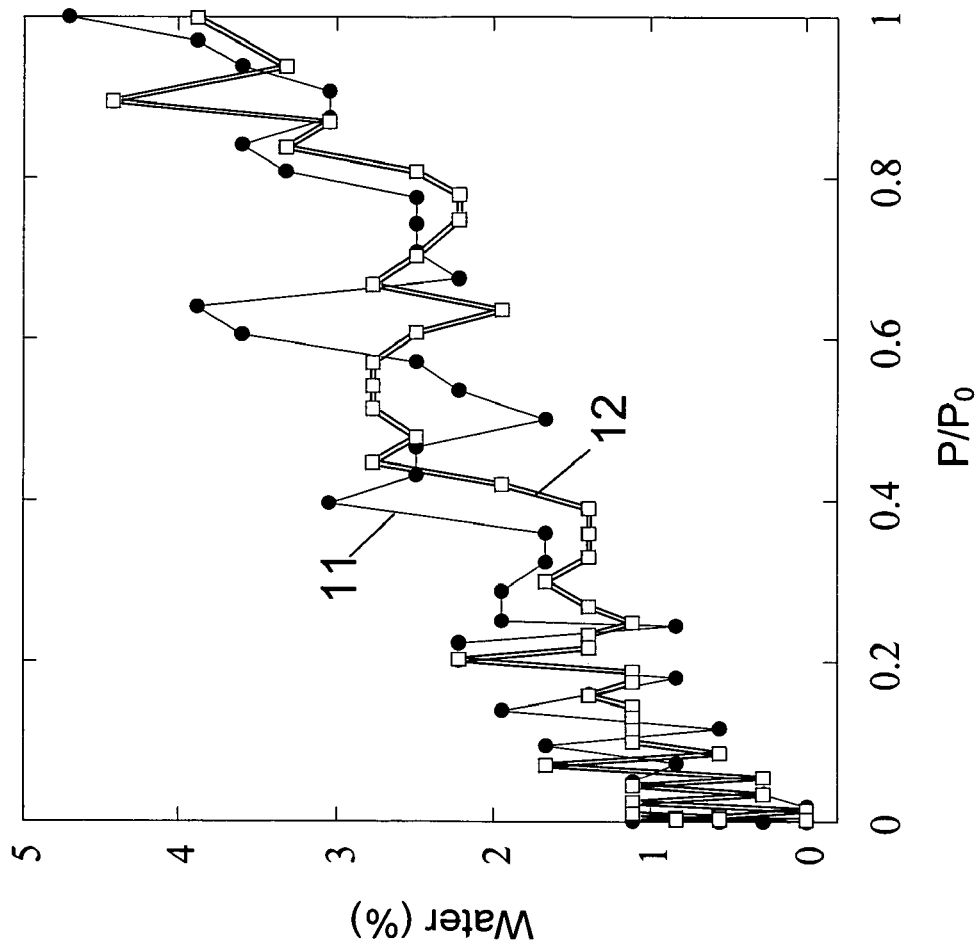
FIGS. 5A to 5E show adsorption/desorption isotherms for (A) pristine material, (B) a SiOC(H) low-k material (NCS) after $CF_4/O_2$ plasma etch, (C) a SiOC(H) low-k material (NCS) after $C4F_8$ plasma etch, (D) a SiOC(H) low-k material (NCS) after CF4 standard plasma etch, (E) a SiOC(H) low-k material (NCS) after hexamethyldisilizane (HMDS) treatment.

FIG. 5A shows the amount of water adsorbed in an undamaged reference low-k material, also referred to as pristine material. Insignificant water adsorption in the reference material (in this example, pristine material) occurs without bulk condensation and reflects only the presence of a small amount of water adsorption centers. If the number of these centers is limited, the contact angle remains high because the adsorbed water molecules do not form a continuous layer on the wall surface. FIG. 5A shows that the film adsorbs only 4% of water in respect to the film volume.

Figure 5B:
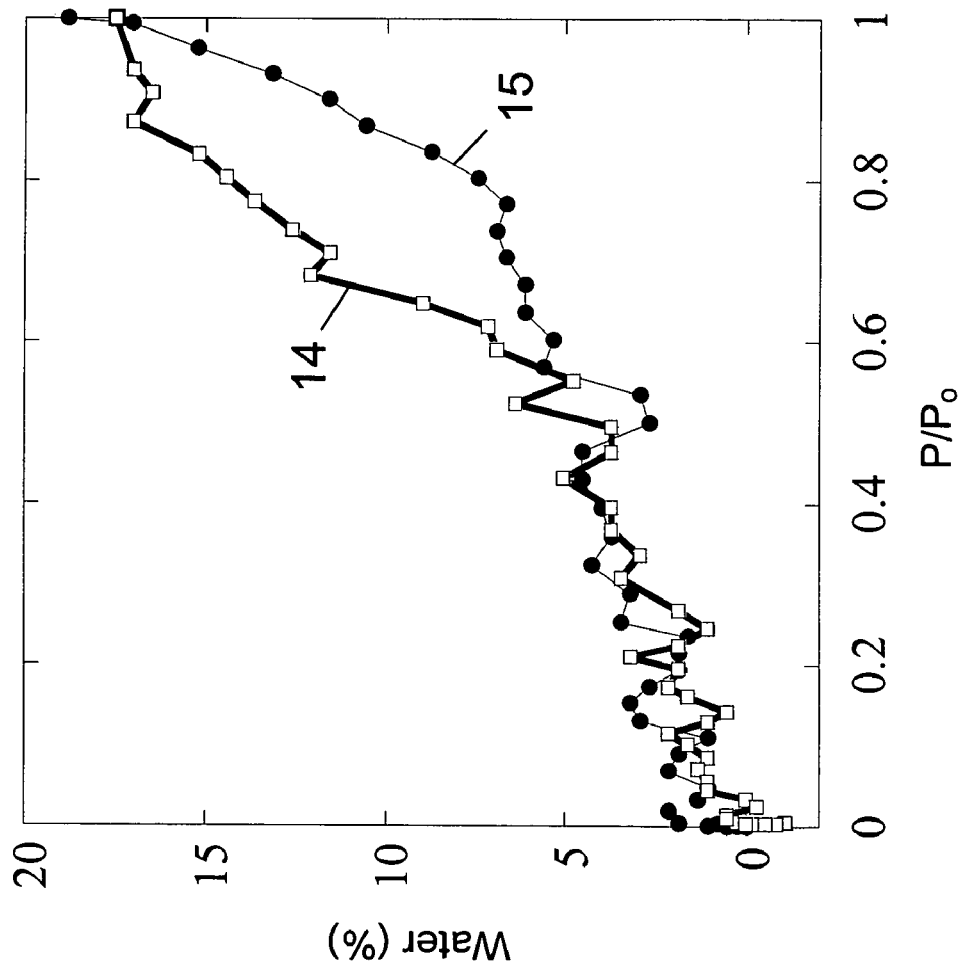

FIG. 5B shows the amount of water absorbed in a SiOC(H) low-k material (NCS) after $CF_4/O_2$ plasma etch. The amount of water absorbed in the low-k film due to plasma damage is 18%.

Figure 5C:
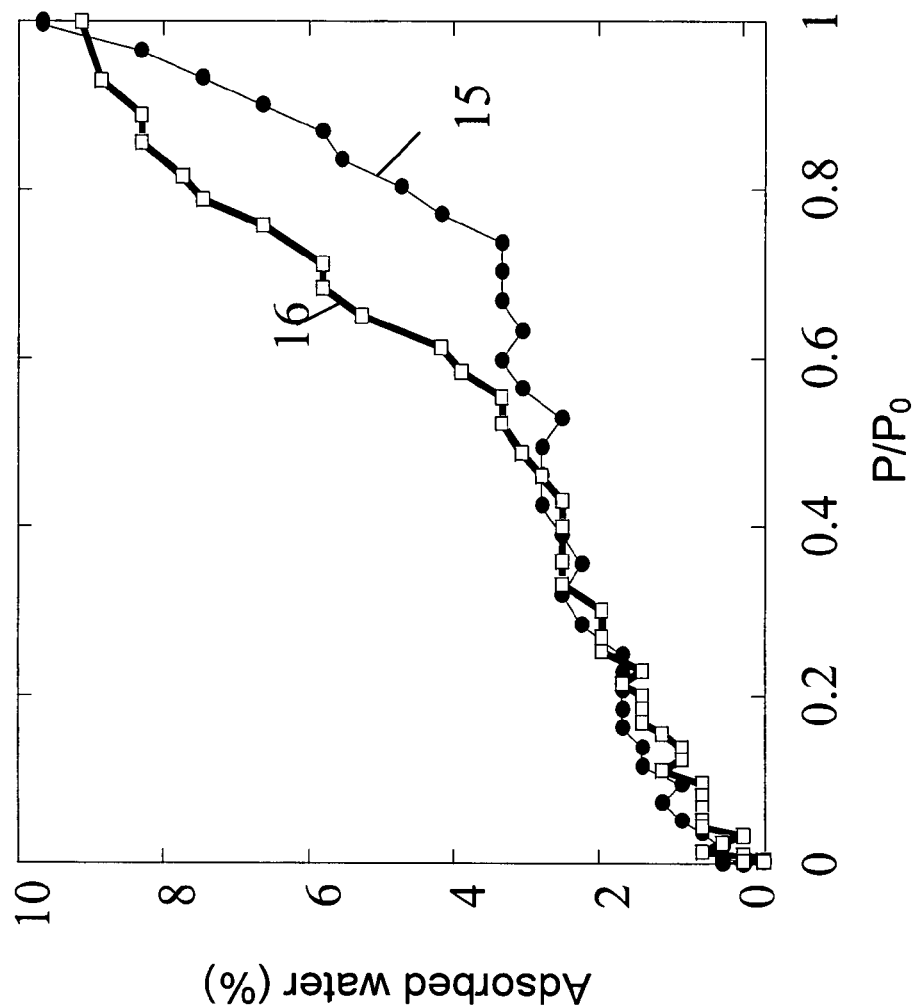

FIG. 5C shows the amount of water absorbed in a SiOC(H) low-k material (NCS) after $C_4F_8$ plasma etch. The amount of water absorbed in the low-k film due to plasma damage is 9.5%.

Figure 5D:
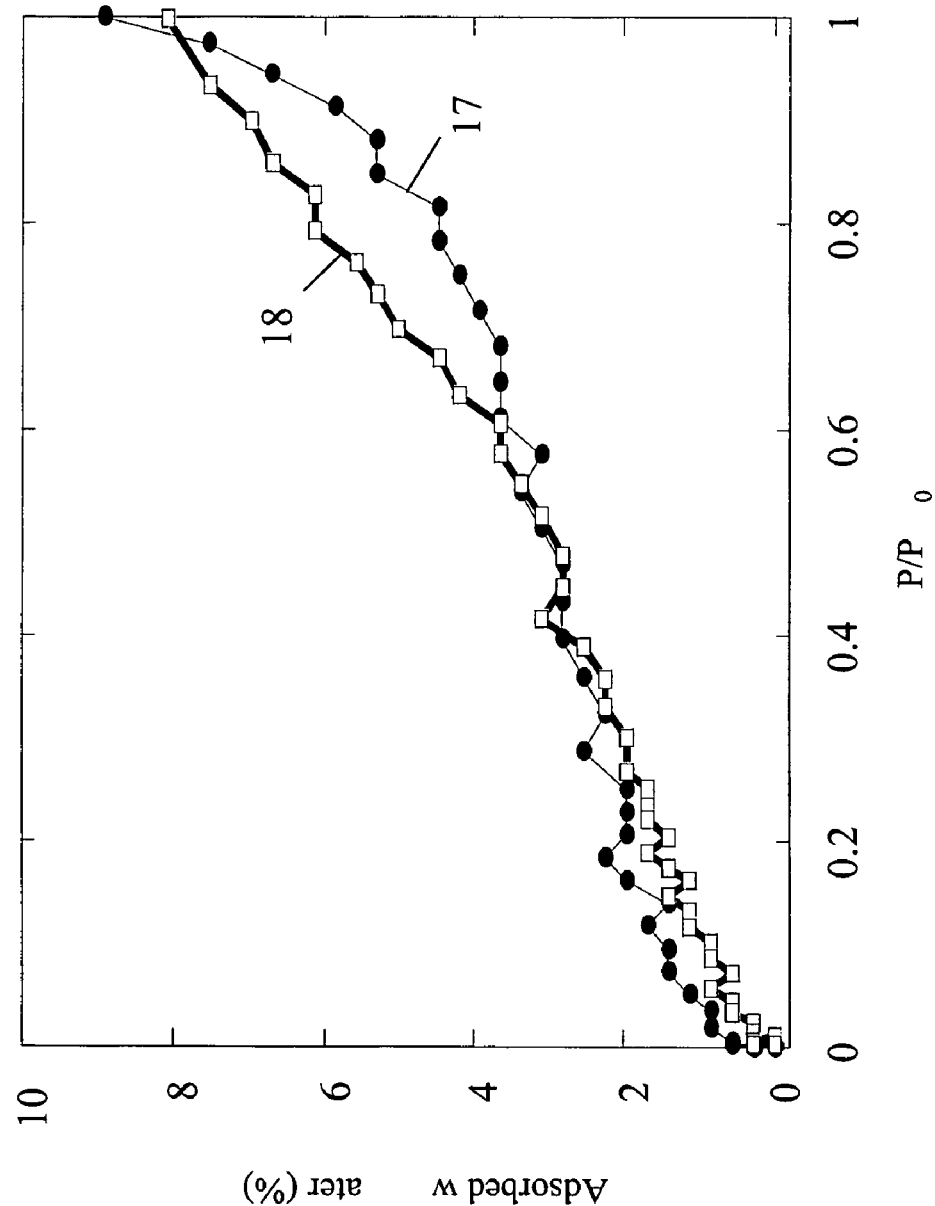

FIG. 5D shows the amount of water absorbed in a SiOC(H) low-k material (NCS) after $CF_4$ standard plasma etch. The amount of water absorbed in the low-k film due to plasma damage is 9%.

Figure 5E:
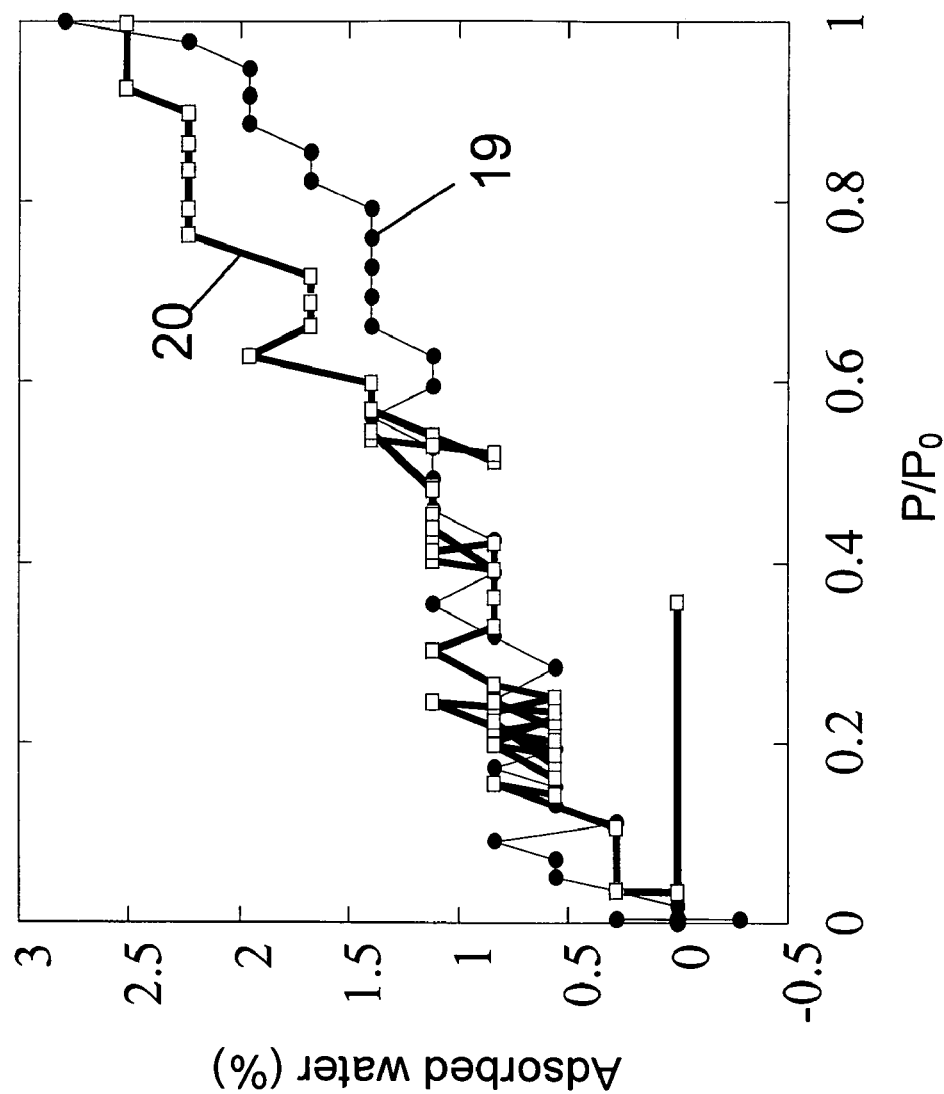

FIG. 5E shows the amount of water absorbed in a SiOC(H) low-k material (NCS) after HMDS treatment. The amount of water absorbed in the low-k film due to plasma damage is 2.7%.

Example 2

Determination of the Degree and Depth of Damage in a Porous Low-k Film

A porous low-k material deposited onto a wafer is subjected to a standard etch process for anisotropically etching vias and trenches for interconnect processing (e.g., to create (dual) damascene structures). The etch plasma used in this example includes $CF_4$, $O_2$, $N_2$ and Ar.

Using the methods described above and the following equation, the depth of damage within a low-k film can be obtained:

$$P_{a2,2} * d_0 = P_{a1} * d + P_{a2,1} * (d_0 - d) \tag{11}$$

where $P_{a2,2}$ is the porosity of the damaged low-k film measured using the second adsorptive, for example, water; $P_{a2,1}$ is porosity of the low-k film before damage (measured using the second adsorptive); $P_{a1}$ is porosity of the undamaged low-k film measured using the first adsorptive, for example, toluene; $d_0$ is the film thickness and d is the depth of wetting. The value $P_{a1}$ is obtained from the first ellipsometric measurement performed on the low-k film with the first adsorptive, such that the porosity and/or pore size of the low-k film can be obtained. The value $P_{a2,2}$ is obtained from the second ellipsometric measurement performed on the damaged low-k film with the second adsorptive. The value $P_{w1}$ is obtained from the third ellipsometric measurement performed on the undamaged low-k film (e.g., before plasma etch and/or strip) with the second adsorptive.

Results of the ellipsometric measurements gave a $P_{a2,2}$ value of 14.2%, a $P_{a2,1}$ value of 4.2% and a $P_{a1}$ value of 30%. By using the Lorentz-Lorentz equation:

$$\frac{n_{r1}^2 - 1}{n_{r1}^2 + 2} = V \frac{n_{ads}^2 - 1}{n_{ads}^2 + 2} + (1 - V) \frac{n_2^2 - 1}{n_2^2 + 2} \tag{12}$$

wherein V is the volume of adsorbed water, and $n_{r1}$, $n_{ads}$ and $n_2$ are, respectively, refractive indices of the film with adsorbed water, water and the film itself. By dividing the value obtained by equation (12) by the volume of the film and multiplying this by 100, a damage of 38.5% is obtained. This indicates that 38.5% of the total low-k film thickness is damaged.

CONCLUSION

Various arrangements and embodiments have been described herein. It will be appreciated, however, that those skilled in the art will understand that changes and modifications may be made to these arrangements and embodiments without departing from the true scope and spirit of the present invention, which is defined by the following claims.

The invention claimed is:

1. A method for the quantification of hydrophilic properties of a porous material, the method comprising:

performing a first ellipsometric measurement on the porous material using a first adsorptive having a first wetting angle;

performing a second ellipsometric measurement on the porous material using a second adsorptive having a second wetting angle, wherein the first and second wetting angles are different towards the porous material; and determining the hydrophilic properties of the porous material based, at least in part, on the first and second ellipsometric measurements.

2. The method of claim 1, wherein the first wetting angle is substantially zero and the second wetting angle is substantially different from zero.

3. The method of claim 1, further comprising performing a third ellipsometric measurement on the porous material before damage treatment, the third ellipsometric measurement being made using the second adsorptive.

4. The method of claim 3, wherein the hydrophilic properties of the porous material are determined based, at least in part, on the first, second and third ellipsometric measurements, and the method further comprises determining a measure for a depth of damage of the porous material from the hydrophilic properties.

5. The method of claim 1, wherein the first wetting angle is one of (i) smaller than 5°, (ii) smaller than 3° and (iii) smaller than 1°.

6. The method of claim 1, wherein the first adsorptive is one of nitrogen, toluene, methanol and benzene.

7. The method of claim 1, wherein the second wetting angle is 90° or higher.

8. The method of claim 1, wherein the second adsorptive comprises polar molecules.

9. The method of claim 8, wherein the second adsorptive is one of water, $SOCl_2$ and an inorganic solvent.

10. The method of claim 1, wherein the porous material is a low-k material.

* * * * *